US008543069B2

(12) United States Patent  (10) Patent No.: US 8,543,069 B2
Kari et al.  (45) Date of Patent: Sep. 24, 2013

(54) SYSTEMS, METHODS AND APPARATUS FOR AUXILIARY ETHERNET PORT FOR WIRELESS PORTABLE X-RAY DETECTOR

(75) Inventors: Nirmal Mukund Kari, Waukesha, WI (US); Scott William Petrick, Sussex, WI (US); Christopher Unger, Brookfiled, WI (US)

(73) Assignee: General Electric Company, Schenectady, NY (US)

( * ) Notice: Subject to any disclaimer, the term of this patent is extended or adjusted under 35 U.S.C. 154(b) by 2131 days.

(21) Appl. No.: 11/461,760

(22) Filed: Aug. 1, 2006

(65) Prior Publication Data

US 2008/0029707 A1  Feb. 7, 2008

(51) Int. Cl.
*H04B 1/40* (2006.01)
*H04B 7/00* (2006.01)
*G01T 1/24* (2006.01)
*H01L 25/00* (2006.01)
*H01L 27/00* (2006.01)
*H01L 27/146* (2006.01)

(52) U.S. Cl.
USPC .................. 455/74.1; 455/66.1; 250/370.09

(58) Field of Classification Search
None
See application file for complete search history.

(56) References Cited

U.S. PATENT DOCUMENTS

| | | | |
|---|---|---|---|
| 4,692,806 A * | 9/1987 | Anderson et al. | 375/240.08 |
| 5,708,840 A | 1/1998 | Kikinis et al. | |
| 5,737,491 A * | 4/1998 | Allen et al. | 704/270 |
| 5,909,478 A * | 6/1999 | Polichar et al. | 378/98.2 |
| 6,131,040 A * | 10/2000 | Knuutila et al. | 455/550.1 |
| 6,205,199 B1 * | 3/2001 | Polichar et al. | 378/98.8 |
| 6,337,712 B1 | 1/2002 | Shiota et al. | |
| 6,440,072 B1 | 8/2002 | Schuman et al. | |
| 6,475,146 B1 | 11/2002 | Frelburger et al. | |
| 6,833,867 B1 | 12/2004 | Anderson | |
| 7,022,075 B2 | 4/2006 | Grunwald et al. | |
| 2003/0078072 A1 | 4/2003 | Serceki et al. | |
| 2003/0106067 A1 * | 6/2003 | Hoskins et al. | 725/119 |
| 2004/0114725 A1 * | 6/2004 | Yamamoto | 378/189 |
| 2005/0136892 A1 | 6/2005 | Oesterling et al. | |
| 2005/0165911 A1 * | 7/2005 | Homiller | 709/219 |
| 2005/0197093 A1 | 9/2005 | Wiklof et al. | |
| 2005/0202844 A1 * | 9/2005 | Jabri et al. | 455/556.1 |
| 2005/0273366 A1 * | 12/2005 | Ohara | 705/3 |
| 2006/0070384 A1 | 4/2006 | Ertel | |
| 2007/0004980 A1 | 1/2007 | Warner et al. | |
| 2007/0140424 A1 * | 6/2007 | Serceki | 378/62 |
| 2007/0180046 A1 | 8/2007 | Cheung et al. | |
| 2007/0269010 A1 | 11/2007 | Turner | |

OTHER PUBLICATIONS

Frazier Howard, "The 802.3z Gigabit Ethernet Standard,"printed Jun. 25, 1998., IEEE Standards Board, p. 6.*
Chen Alice, "Multimedia Applications in a Mobile ATM Environment", printed Aug. 1998., IEEE Standards Board, p. 8.*
Broadcom press release # 659800, "Broadcom, HP and Linksys Make Wi-Fi Installation as Easy as Pushing a Button," printed Dec. 16, 2005.
Broadcom press release #682849, "Broadcom makes Wi-Fi Phone Installation as Easy as Pushing a Button," printed Dec. 16, 2005.

* cited by examiner

*Primary Examiner* — Yuwen Pan
*Assistant Examiner* — Ayodeji Ayotunde (57) ABSTRACT

Systems, methods and apparatus are provided through which a portable imaging device is operable to communicate to other devices through both a wired communication path and a wireless communication path.

23 Claims, 6 Drawing Sheets

SYSTEMS, METHODS AND APPARATUS FOR AUXILIARY ETHERNET PORT FOR WIRELESS PORTABLE X-RAY DETECTOR

FIELD OF THE INVENTION

This invention relates generally to portable X-ray detectors, and more particularly to transmission of data to and from the portable X-ray detectors.

BACKGROUND OF THE INVENTION

Digital medical diagnostic imaging systems can be operably coupled to a portable X-ray detector through a wireless communication path. Where the portable X-ray detector is operably coupled to a digital medical diagnostic imaging system through a wireless communication path, the portable X-ray detector is often referred to as a wireless portable X-ray detector.

A wireless portable X-ray detector facilitates patient positioning with ease for the patient while also relieving the X-ray radiologist from wielding a cumbersome and heavy tether. However, the wireless communication path between the wireless portable X-ray detector presents at least three problems One problem of a wireless portable X-ray detector is that bandwidth of the data transmitted through the wireless communication path is limited by the bandwidth of the wireless protocol. The bandwidth of the wireless communication path is an order of a magnitude smaller than that attainable using a wired connection. For example a wireless communication path using 802.11 protocol has a bandwidth of 54 mbps in comparison to a wired communication path using 802.3z Gigabit Ethernet™ protocol has a bandwidth of 1000 mbps. In that example the wired communication path is nearly twenty times faster than the wireless communication path. The limited bandwidth of the wireless communication path between the portable results in an increase of image latency, especially for applications that require large amounts of data at high frame rates. The increased latency of a wireless communication path greatly reduces the use of advanced applications and imaging frame rates that require high bandwidth.

A second problem of a wireless communication path between a wireless portable X-ray detector and a digital medical diagnostic imaging system is a problem of any wireless device, which is limited battery charge longevity. The loss of battery power can be especially problematic when the battery runs out in the middle of a medical imaging procedure without having completed acquisition and transmission of all of the image data from the wireless portable X-ray detector to the digital medical diagnostic imaging system.

A third problem of a wireless communication path between a wireless portable X-ray detector and a digital medical diagnostic imaging system is diagnosis and maintenance of the wireless communication path when the wireless communication path fails. When the wireless communication path fails, diagnosis and/or maintenance of the wireless communication path can be difficult if not nearly impossible.

To alleviate the problems of wireless portable X-ray detectors, some X-ray facilities implement two X-ray detectors, a wireless portable X-ray detector and a wired X-ray detector. However, two X-ray detectors is at least more expensive, if not prohibitively more expensive.

For the reasons stated above, and for other reasons stated below which will become apparent to those skilled in the art upon reading and understanding the present specification, there is a need in the art for increased bandwidth capacity between the portable X-ray detector and the digital medical diagnostic imaging system without purchasing two X-ray detectors. There is also a need to improved battery life of the wireless portable X-ray detector. There is also a need for improved ability to diagnose and maintain the wireless communication path.

BRIEF DESCRIPTION OF THE INVENTION

The above-mentioned shortcomings, disadvantages and problems are addressed herein, which will be understood by reading and studying the following specification.

In one aspect, a portable imaging device includes a processor and a detector connection point that is operably coupled to the processor and operable to communicate data through a wired communication path and the portable imaging device includes a wireless transceiver that is operably coupled to the processor and operable to communicate data with the digital medical diagnostic imaging system through a wireless communication path. The portable image device solves the need in the art for increased bandwidth capacity between the portable imaging device and an external device, the need to improve battery life of the portable imaging device and the need to improve ability to diagnose and maintain a wireless communication path to the portable imaging device.

In another aspect, an imaging system includes a digital medical diagnostic imaging system a portable imaging device that is operable to communicate data with the digital medical diagnostic imaging system through a wired communication path and through a wireless communication path. The imaging system solves the need in the art for increased bandwidth capacity between the portable imaging device and the digital medical diagnostic imaging system, the need to improve battery life of the portable imaging device and the need to improve diagnosis and maintenance of a wireless communication path to the portable imaging device.

In yet another aspect, a method of communicating data between a portable imaging device and a computer includes determining whether a wired communication path is established between the portable imaging device and the computer, upon a condition in which the wired communication path is established, using the wired communication path to communicate data between the portable imaging device and the computer, upon a condition in which the wired communication path is not established, establishing a wireless communication path between the portable imaging device and the computer, and using the wireless communication path to communicate data between the portable imaging device and the computer.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 1 is an overview of an imaging system that includes a portable imaging device that has both a wired communication path and a wireless communication path;

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, apparatus of the system are described. In the third section, methods of using the apparatus are described. In the fourth section, the hardware and the operating environment in conjunction with which the present teachings may be practiced are described. Finally, in the fifth section, a conclusion of the detailed description is provided.

System Level Overview

Figure 1:
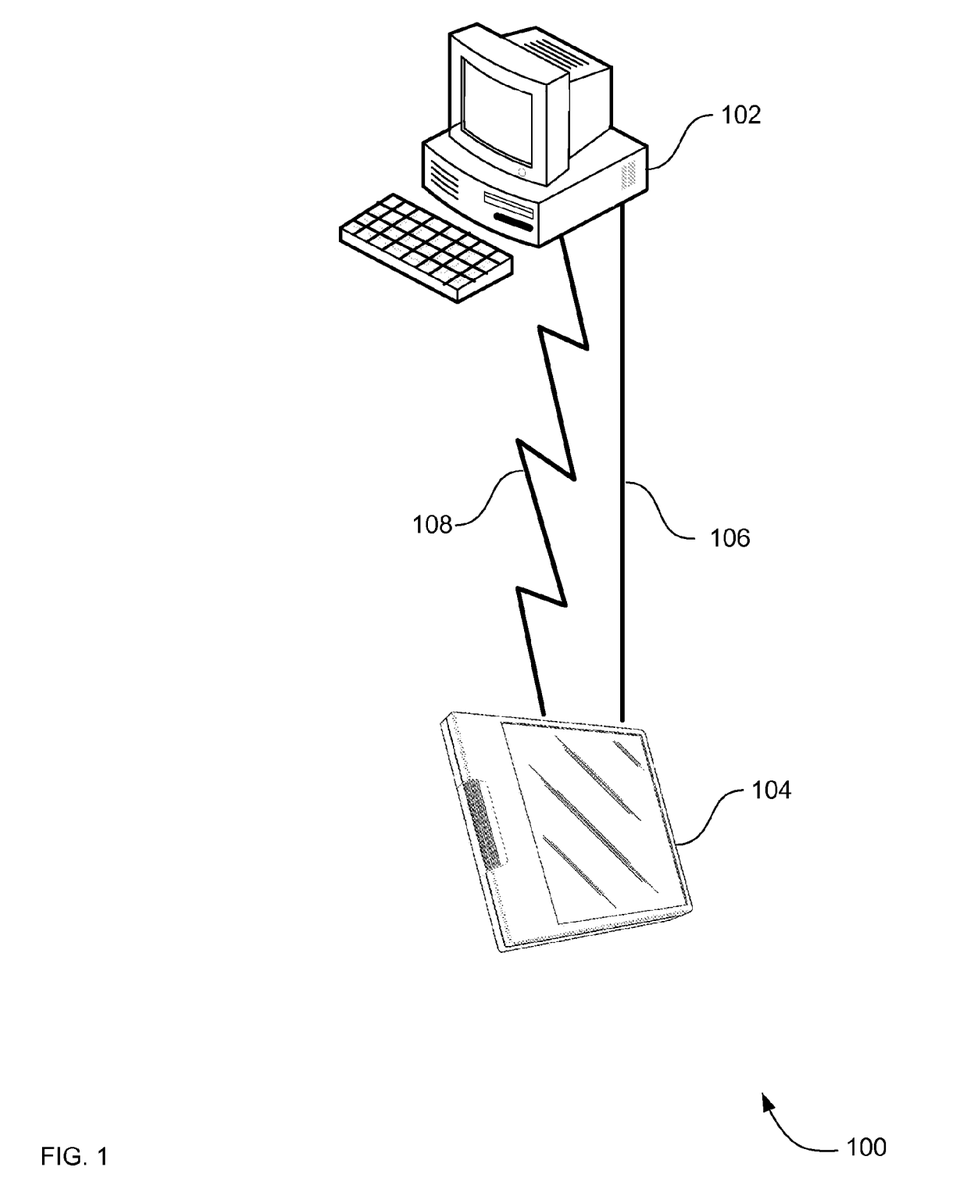
FIG. 1 is a diagram illustrating a system-level overview of an embodiment.

FIG. 1 is an overview of an imaging system 100 that includes a portable imaging device that has both a wired communication path and a wireless communication path. System 100 solves the need in the art for increased bandwidth capacity between the portable X-ray detector and the digital medical diagnostic imaging system without purchasing two X-ray detectors, for improved battery life of the wireless portable X-ray detector and for improved ability to diagnose and maintain the wireless communication path.

System 100 includes a host computer 102 or other electronic device such as a digital medical diagnostic imaging system. System 100 also includes a portable imaging device, e.g., portable X-ray detector 104. Host computer 102 is in communication with portable X-ray detector 104. The communication between host computer 102 and portable X-ray detector 104 can occur in one of three different modes as described below.

In the first mode, a wired-only connection mode, the portable X-ray detector 104 is in direct, wired connection 106 with host computer 102. The wired connection 106 which can include, but is not limited to, a wired Ethernet™ connection. Thus, according to this mode, portable X-ray detector 104 is in wired connection with host computer 102. This direct connection between host computer 102 and portable X-ray detector 104 provides an efficient connection for data exchange between portable X-ray detector 104 and host computer 102, as well as, an efficient connection for the exchange of wireless configuration data between portable X-ray detector 104 and host computer 102. Thus system 100 solves the need in the art for increased bandwidth capacity between the portable X-ray detector 104 and the digital medical diagnostic imaging system without purchasing two X-ray detectors. The wired communication path 106 is also known as a tethered connection.

Furthermore, in some embodiments, the connection 106 between host computer 102 and portable X-ray detector 104 can also provide a direct physical connection between a rechargeable power source of portable X-ray detector 104 and a charging power source. Thus, system 100 solves a need in the art for improved battery life of the wireless portable X-ray detector 104.

In the second mode, wireless mode, e.g., using a wireless communication path, portable X-ray detector 104 is physically detached from host computer 102. In this second mode, portable X-ray detector 104 communicates with host computer 102 through a wireless communication path 108. Alternatively, portable X-ray detector 104 and host computer 102 can communicate directly to one another through an ad hoc wireless communication path. A wireless communication path 108 can be beneficial in certain circumstances, as compared to a direct, wired communication path 106, because the wireless communication path 108 provides for a greater mobility of the portable X-ray detector 104.

In the third mode, the host computer 102 communicates to the portable X-ray detector 104 through both the wireless communication path 108, and the host computer 102 communicates to the portable X-ray detector 104 through the wired communication path 106. Alternatively, portable X-ray detector 104 and host computer 102 can communicate directly to one another through an ad hoc wireless communication path. Simultaneous communication through wireless communication path 108 and a wired communication path 106 can be beneficial in certain circumstances because the wireless communication path provides for a greater mobility of the portable X-ray detector 104, yet the wired communication path 106 provides for faster bandwidth and the direct communication path 106 can provide a power supply to the portable X-ray detector 104.

The third mode, in which the host computer 102 communicates to the portable X-ray detector 104 though both the wireless communication path 108 the wired communication path 106 provides a means to troubleshoot, maintain and service the wireless communication path 108. Thus, system 100 also solves the need in the art for improved ability to diagnose and maintain the wireless communication path 108.

An illustrative portable X-ray detector is described, for example, in conjunction with the description of FIG. 2 below. The use of a portable X-ray detector 104 in the three modes is described, for example, in conjunction with the description of FIGS. 3 and 4 below.

Apparatus Embodiments

Figure 2:
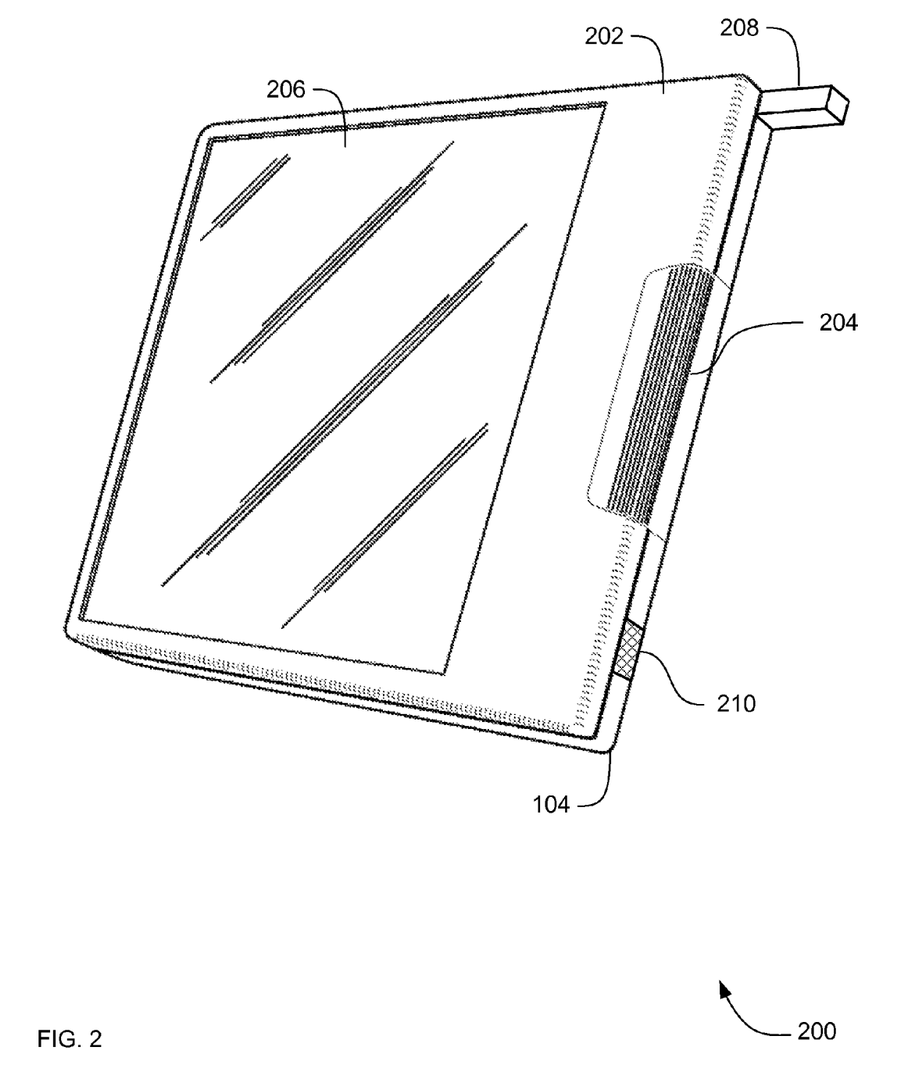
FIG. 2 is a block perspective diagram of portable X-ray detector according to an embodiment having apparatus that is operable to support both direct and wireless communication paths with exterior devices.

FIG. 2 is a block perspective diagram of portable X-ray detector 104 according to an embodiment having apparatus that is operable to support both direct and wireless communication paths with exterior devices. Portable X-ray detector 104 solves the need in the art for increased bandwidth capacity between the portable X-ray detector and the digital medical diagnostic imaging system without purchasing two X-ray detectors, for improved battery life of the wireless portable X-ray detector and for improved ability to diagnose and maintain the wireless communication path.

As described above, portable X-ray detector 104 is one component of portable imaging system 100. Portable X-ray detector 104 includes housing 202, grip 204, digital X-ray detector element 206, antenna 208 and a detector connection point 210. In embodiments where the wired communication path 106 is a wired Ethernet™ connection, the detector connection point is known as an auxiliary Ethernet™ port. In some embodiments the detector connection point 210 is an RJ45 jack (a "Registered Jack-45") which is an 8 wire connector.

Digital X-ray detector element 206 collects X-rays transmitted from an X-ray generator, e.g., through a subject (a patient), and converts the X-rays to an image including a number of pixels. The portable X-ray detector 104 then transfers this image to host computer 102, through either a wired communication path or through a wireless communication path 106, e.g., using antenna 208, as described, for example, in conjunction with the description of FIG. 1, above. By way of example only, the digital X-ray detector element 206 can be about 41 centimeters (cm) square and about one inch thick.

FIG. 2 shows an external antennae 208, but other embodiments that are not shown, can include an internal antennae. FIG. 2 shows an external antennae 208 having a particular location on the portable X-ray detector 104 and a particular physical shape. However, portable X-ray detector 104 is not limited by the depicted location and shape of the external antennae 208. Other embodiments of the location and shape of the external antennae 208 are within the scope of the portable X-ray detector 104.

Portable X-ray detector 104 further includes a power source (not shown). Preferably, the power source is a rechargeable power source, such as a rechargeable battery (not shown), contained within housing 202.

Detector connection point 210, along with a complementary mating connection point on wire communication path 106, which will be described below, form a direct connection between portable X-ray detector 104 and host computer 102. The detector connection point 210 can implement any one of a number of conventional communication protocols, such as USB 2.0, Ethernet™ (e.g. 802.3 Gigabit Ethernet™), firewire (I.E.E.E. 1394), RS-232 Appletalk®. RS-232 connections are the simplest of the aforementioned connections to implement, but provide the lowest data transfer rate.

Further, in this illustrative embodiment in which the power source is a rechargeable battery, detector connection point 210 can also form a direct connection, such as through a USB connection, between portable X-ray detector 104 and a charging power source when portable X-ray detector 104 is attached to host computer 102 through the wired connection 106. The charging of rechargeable batteries is well known and is not described further herein.

Some embodiments of portable X-ray detector 104 include a user-activatable button (not shown). The user-activatable button is an "eject-type" button that a user can physically press when the user wishes to eject the cable of the wired communication path 106 from the detector connection point 210 of the portable X-ray detector 104. Alternatively, other types of user-activatable sensors can be used instead of user-activatable sensor. By way of example only, the user-activatable sensor can be a graphical user interface (GUI) element represented in a portion of display of the host computer 102. Thus, at least the portion of display containing the user-activatable sensor can be touch-sensitive and perform the same functions described above with respect to user-activatable sensor.

Multiple user-activatable sensors may be employed on the portable X-ray detector 104. By way of example only, portable X-ray detector 104 can have a button user-activatable sensor, as well as, a touch-sensitive sensor on the display. Each of these user-activatable sensors can be used independently of one another in that user activation of either user-activatable sensor initiates decoupling of the cable of the wired communication path 106 from the detector connection point 210 of the portable X-ray detector 104. In other words, a user can either press the button or touch the display to eject the cable of the wired communication path 106 from the detector connection point 210 of the portable X-ray detector 104.

Alternatively, the sending of the wireless operating parameters to portable X-ray detector 104 can be initiated when portable X-ray detector 104 is first attached to the wired communication path 106. Furthermore, the wired communication path 106 can be used to configure the wireless port during routine periodic configuration, dealing with parameters such as encryption keys and access channel assignments. In this case, a user-activatable sensor is not needed to signal imminent detaching of the cable of the wired communication path 106 from the detector connection point 210 of the portable X-ray detector 104. However, the user should take care not to disconnect the cable of the wired communication path 106 from the detector connection point 210 of the portable X-ray detector 104 until the configuration is complete, which under normal operating conditions takes no longer than about 0.5 second.

Figure 3:
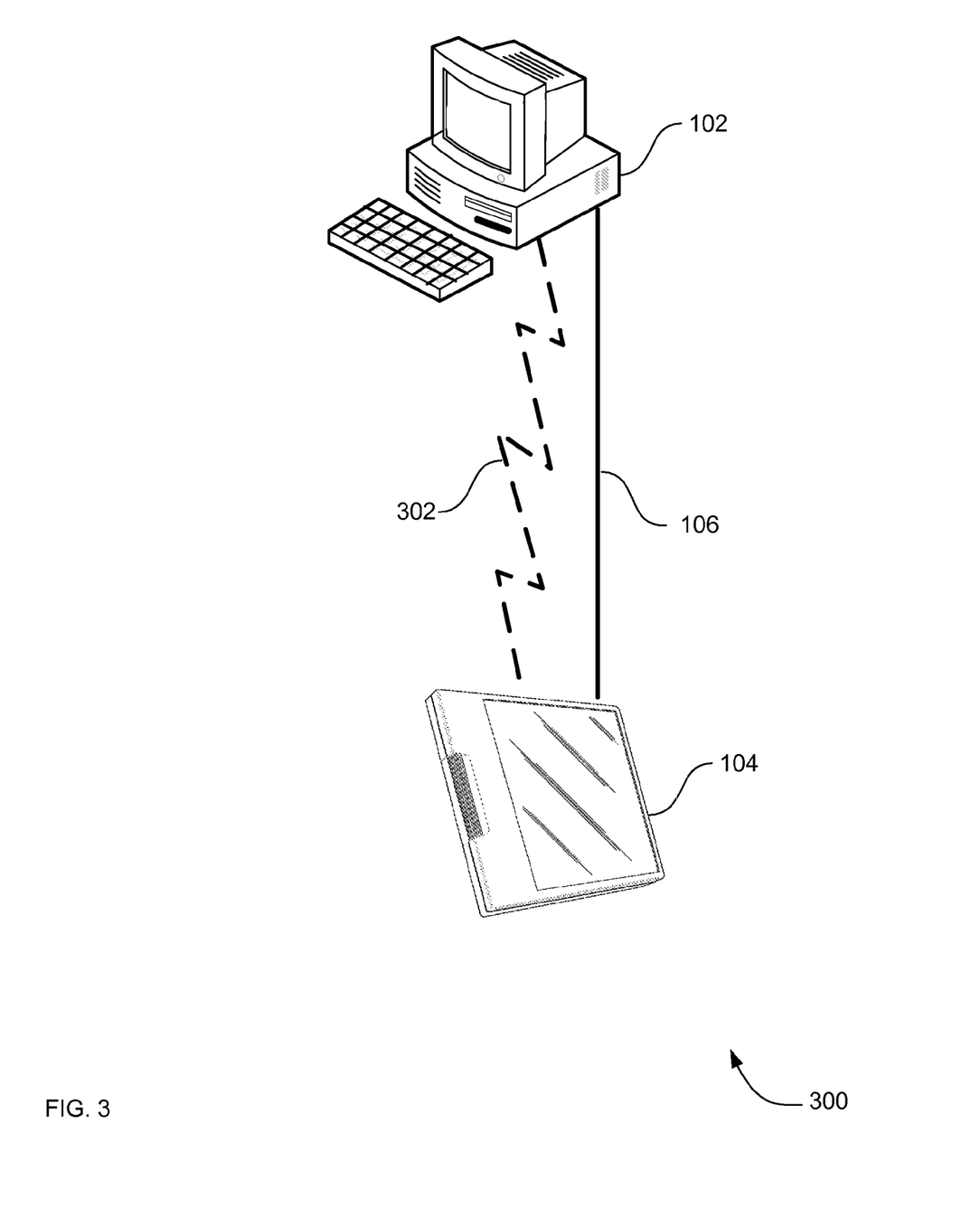
FIG. 3 is a block diagram of an imaging system that includes a portable imaging device that is operable to support both direct and wireless communication paths with exterior devices, but in which only the wired connection is in operation and the wireless communication path is disabled.

FIG. 3 is a block diagram of an imaging system 300 that includes a portable imaging device that is operable to support both direct and wireless communication paths with exterior devices, but in which only the wired connection is in operation and the wireless communication path is disabled. System 300 solves the need in the art for increased bandwidth capacity between the portable X-ray detector and the digital medical diagnostic imaging system without purchasing two X-ray detectors, for improved battery life of the wireless portable X-ray detector.

As described above in FIG. 1 and FIG. 2, a direct, wired communication path is initiated between the portable X-ray detector 104 and host computer 102 through detector connection point 210. In FIG. 3, a wireless communication path 302 is operable, but temporarily disabled and deactivated.

Furthermore, in some embodiments, the wired communication path 106 can be operated in two manners, advanced application mode and/or service mode, as described in detail below.

The advance application mode of operation of the portable X-ray detector 104 is beneficial to users who use applications that require data transfer at high speeds, such as for cardiac, angioplasty or tomography applications. The portable X-ray detector 104 can switch to and operate in an advanced application mode.

In some embodiments, the switching can include sensing a presence of a wired link, which is assigned beforehand to a higher priority or "preference." Wireless is only used if a wired link does not exist. In some situations the detector periodically polls the wired link to see if it can be re-established once the wired link becomes inactive or "disappears."

The portable X-ray detector 104 will then disable or deactivate the wireless communication path, and will perform all the advanced applications that require higher bandwidth and greater power consumption using the wired communication path 106. The higher bandwidth is a significant benefit during operations of the portable X-ray detector 104 for cardiac, angioplasty or tomography imaging.

The service mode of operation of the portable X-ray detector 104 is useful when troubleshooting or configuring the wireless communication path 108. Service ability is a major concern for a portable X-ray detector 104 that has only a wireless port especially if the failure is in the wireless communication path 108. In service mode the connection point 210 will allow a field engineer to use his lap-top to connect to the portable X-ray detector 104 and upload service information such as environmental monitoring logs, accelerometer logs (to detect drops), voltage and sensor readings, error codes and exception messages from the processor of the portable X-ray detector 104, built-in self test results, the state of the wireless connection, and retrieve any images stored in the detector non-volatile memory. In some embodiments, the portable X-ray detector 104 can also download through the connection point 210 a new firmware or software image with a new feature, bug fix or an upgrade.

An important point for success in the service mode is intelligent power management. If the portable X-ray detector 104 is to be used in an exclusively wireless mode, such as described in FIG. 4 below, then power management will be required to consume as minimal power as possible by disabling the connection point 210 hardware circuitry while in wireless mode. The service mode can be initiated via the system. In some embodiments, the service mode is initiated through a built-in service mode which is accessed from a link on the user GUI. The service mode can be automatically initiated when the portable X-ray detector 104 detects that a laptop of a field engineer is connected to detector connection point port 210. If the detector connection point 210 has a power line, then the portable X-ray detector 104 can be charged while undergoing service simultaneously. As part of field diagnostics, communication can be "looped" through the portable X-ray detector 104 passing into the detector through the detector connection point 210 and out of the portable X-ray detector 104 on the wireless port (and visa versa) in order to verify communication integrity; something that can not be done as thoroughly with a single port of the portable X-ray detector 104.

As described above, if portable X-ray detector 104 is powered by a rechargeable battery, the direct communication path 106 can provide a direct connection between portable X-ray detector 104 and a charging power source. The recharging power source can derive its own power from host computer 102. For example, some wired connections include power connections. Examples include, but are not limited to, USB and Ethernet™ connections through which host computer 102 can provide power to portable X-ray detector 104 for charging the rechargeable power source.

Figure 4:
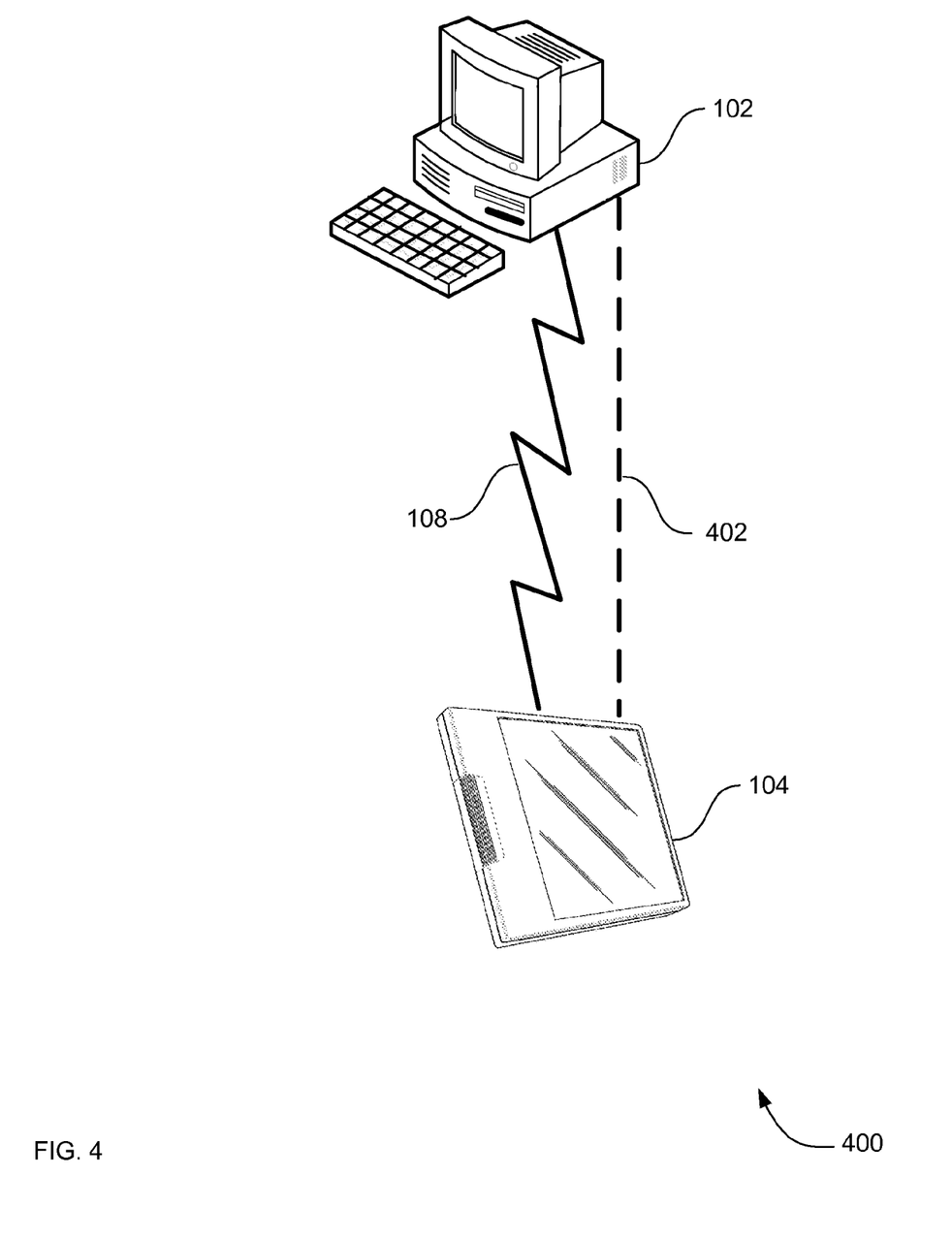
FIG. 4 is a block diagram of an imaging system that includes a portable imaging device that is operable to support both direct and wireless communication paths with exterior devices, but in which only the wireless communication is in operation and the wired communication path is disabled.

FIG. 4 is a block diagram of an imaging system 400 that includes a portable imaging device that is operable to support both direct and wireless communication paths with exterior devices, but in which only the wireless communication is in operation and the wired communication path is disabled. Imaging system 400 solves the need in the art for improved battery life of a wireless portable X-ray detector.

As described above in FIG. 1 and FIG. 2, a wireless communication path 108 is initiated between the portable X-ray detector 104 and host computer 102. In FIG. 4, a wired communication path 402 is operable, but temporarily disabled and deactivated.

For exclusive use in a low bandwidth application such as a single shot RAD procedure, the portable X-ray detector 104 can operate in a true "Wireless Mode." Power management of the portable X-ray detector 104 is used to disable the detector connection point 210 and associated hardware so as to consume as little of the battery life as possible. The detector connection point 210 will still be useful when the battery low indicator is turned on. If a tether (e.g. a communication cable) for the detector connection point 210 includes a power line then the batteries can be recharged during operation of the portable X-ray detector 104, such as while the X-ray radiologist continues to acquire x-ray images, without any interruption due to power problems.

Method Embodiments

Figure 5:
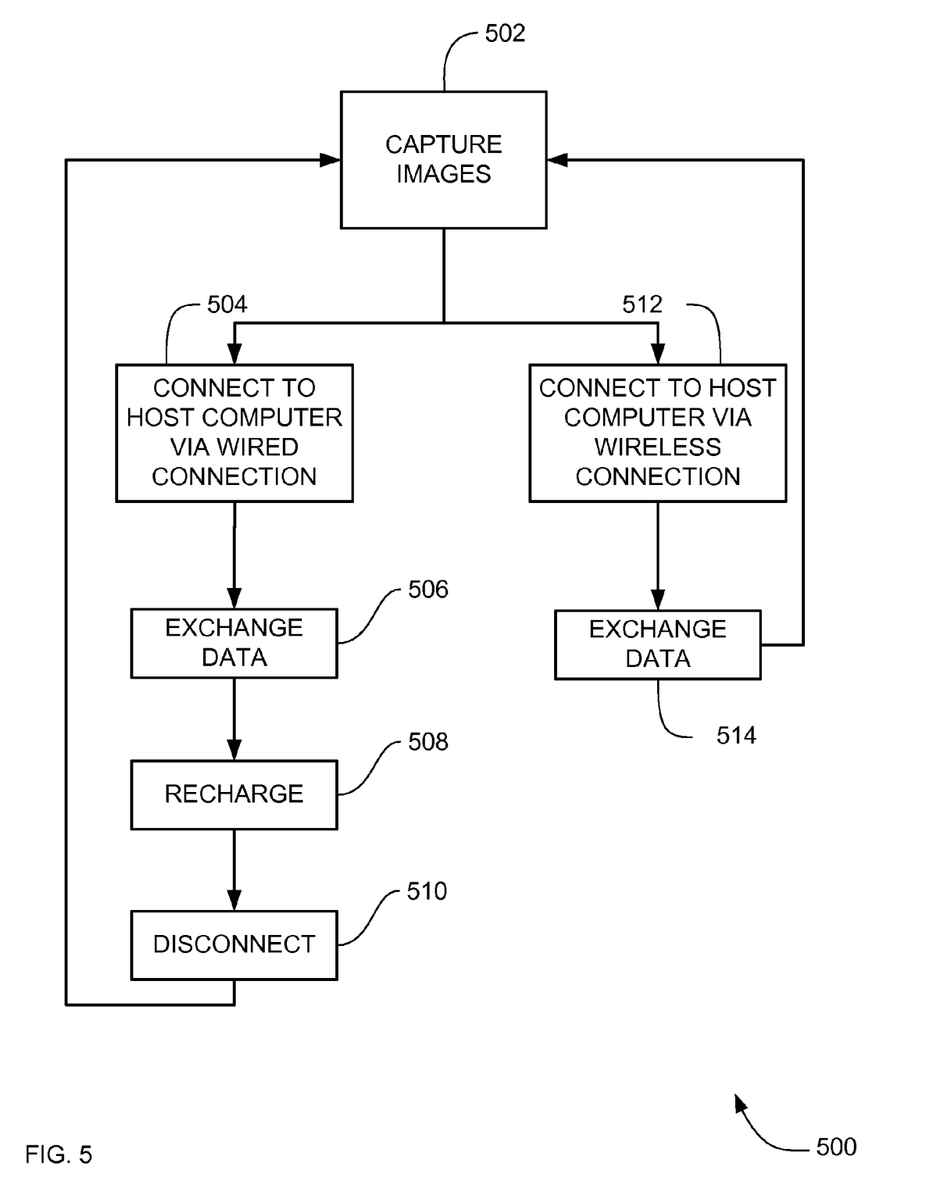
FIG. 5 is a flowchart of a method for using portable X-ray detector.

FIG. 5 is a flowchart of a method 500 for using portable X-ray detector 104. In action 502, portable X-ray detector 104 is used to capture images. Specifically, as described above, portable X-ray detector 104 collects X-rays from an X-ray generator that are passed through a subject, e.g., a patient, and converts the collected X-rays into an image of the subject.

Once the images are captured, portable X-ray detector 104 and host computer 102 cooperate to establish a connection therebetween. In some embodiments, operation of the detector is synchronized with the other components of the X-ray imaging system before the imaging is performed. In some embodiments, the detector verifies existence and/or availability of the wired link prior to pushing image data. If available, the wired communication path is used, if not, then the wireless communication path is used. As described in conjunction with FIG. 1, this connection is made in one of two ways, either wirelessly in action 512 or through a direct, wired connection via wired communication path 106 to host computer 102 in action 504.

In method 500, portable X-ray detector 104 initiates a wireless connection in action 512 whenever data is ready to send to host computer 102 and portable X-ray detector 104 fails to connect through detector connection point 210.

When the connection is wireless, data relating to the images captured, e.g., image data, as well as, data relating to the operating parameters of the wireless connection can be exchanged between host computer 102 and portable X-ray detector 104 in action 514.

When the connection is a direct connection made via wired communication path 106 connected to host computer 102, as in action 504, any of a number of functions may be performed. Namely, image data and operating parameter data can be exchanged between portable X-ray detector 104 and host computer 102 in action 506. The rechargeable power source of portable X-ray detector 104 can be charged in action 508. Once the desired functions are performed and at the convenience of the user, portable X-ray detector 104 can be disconnected from the wired communication path 106 in action 510.

With regard to image data, the images captured by portable X-ray detector 104 typically include high-resolution images, for example, those images having an average size of about eight Mbytes, e.g., including 2048×2048 pixels at 16-bits per pixel. Using a wireless connection, the rate of transfer of these high-resolution images to host computer 102 is considerably slower than with a wired connection (for example, the current 802.11a technology can transfer data at a rate of 54 megabits per second (Mbps)) while current copper Ethernet™ can transfer data at a rate of up to one (1) gigabit per second, i.e., nearly 200 times as fast. However, advances in wireless technology, for example, attaining wireless data transfer rates for an eight Mbyte of about two seconds, will make such wireless applications more practical.

In contrast, using the Ethernet™ connection described above, an eight Mbyte image is transferred from portable X-ray detector 104 to host computer 102 in less than $\frac{1}{10}$th of a second. Thus, for greater efficiency, the transfer of high-resolution images can be withheld during wireless data transfer, and saved in a memory of portable X-ray detector 104 (e.g., see FIG. 6, described below) until portable X-ray detector 104 is attached to wired communication path 106 and a direct, wired connection to host computer 102 is made. For quality assurance purposes, a subset of the image data (reduced number of images, reduced spatial resolution, or lower pixel bit depth (e.g. gray scale resolution)) can be transferred nearly immediately. Nearly immediate transfer can be accomplished over either link the wired communication path or the wireless communication path. The remainder of the image data can be transferred advantageously during the time between patients. If the detector is docked between patients the bulk of image transfer can take place over a wired connection. If not, the wireless connection can still take advantage of the time between patients to transfer the majority of the image data. In either, case the clinician will have enough immediate feedback to know whether the required images have been captured successfully, considering all parameters, including positioning and X-ray technique. It is important to note that the data rate of the direct, wired connection depends upon the type of connection employed. For example USB1.1 has a raw data rate of 11 Mbps, whereas a 1200 baud RS-232 link is significantly slower. A 100BT Ethernet™ link is almost ten times faster than USB1.0, but USB2.0 is almost five times faster than 100BT Ethernet™.

At least a portion of the operating parameter data exchanged between portable X-ray detector 104 and host computer 102 relates to the wireless connection that is shared between portable X-ray detector 104 and host computer 102 which can include, but is not limited to, operating frequency, encryption keys and network identification. For example, one operating parameter configures the wireless protocol being used. Namely, an 802.11 link can be established on a number of different channels with the 2.4 gigahertz (GHz) and 5.8 GHz bands. Host computer 102 can send configuration data to portable X-ray detector 104, causing portable X-ray detector 104 to communicate on a specific one of these channels. Additionally, if encryption is used, host computer 102 can send the keys to portable X-ray detector 104 to cause portable X-ray detector 104 to use those keys for secure communication.

When portable X-ray detector 104 includes a rechargeable battery and the connection to host computer 102 is made via wired communication path 106, a connection can also be made between the rechargeable battery and a charging power source in action 508. Alternatively, portable X-ray detector 104 can include a non-rechargeable power source, such as a disposable battery, obviating such charging.

Hardware and Operating Environment

Figure 6:
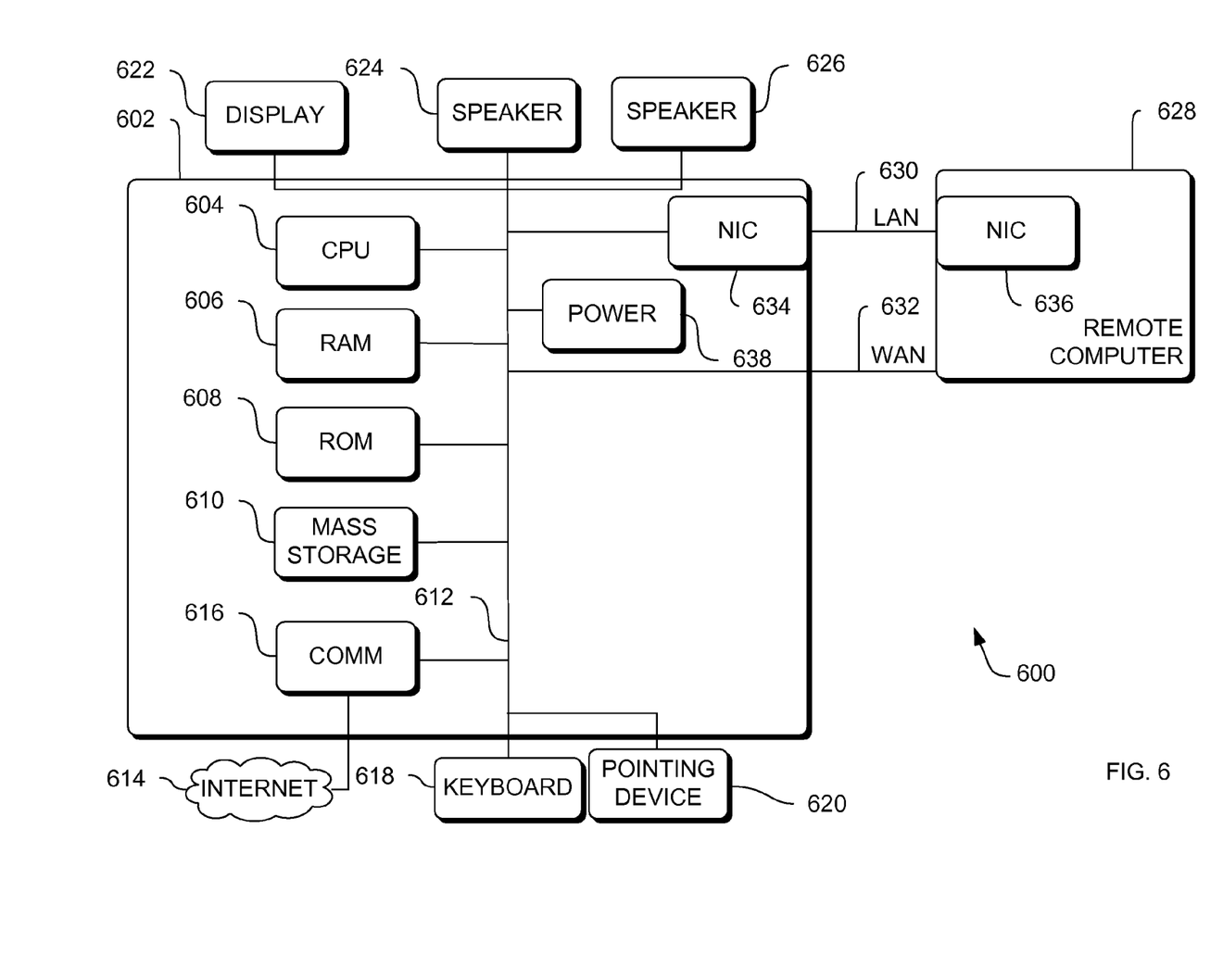
FIG. 6 is a block diagram of hardware and operating environment in which portable imaging can be practiced.

FIG. 6 is a block diagram of hardware and operating environment 600 in which portable imaging can be practiced. The description of FIG. 6 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Host computer 602 includes a processor 604, commercially available from Intel, Motorola, Cyrix and others. Host computer 602 also includes random-access memory (RAM) 606, read-only memory (ROM) 608, and one or more mass storage devices 610, and a system bus 612, that operatively couples various system components to the processing unit 604. The memory 606, 608, and mass storage devices 610 are types of computer-accessible media. Mass storage devices 610 are more specifically types of nonvolatile computer-accessible media and can include one or more hard disk drives, floppy disk drives, optical disk drives, and/or tape cartridge drives. The processor 604 executes computer programs stored on the computer-accessible media. Host computer is one embodiment of host computer 102 in FIG. 1.

Host computer 602 can be communicatively connected to the Internet 614 via a communication device 616. Internet 614 connectivity is well known within the art. In one embodiment, a communication device 616 is a modem that responds to communication drivers to connect to the Internet via what is known in the art as a "dial-up connection." In another embodiment, a communication device 616 is an Ethernet™ or similar hardware network card connected to a local-area network (LAN) that itself is connected to the Internet via what is known in the art as a "direct connection" (e.g., T1 line, etc.).

A user enters commands and information into the host computer 602 through input devices such as a keyboard 618 or a pointing device 620. The keyboard 618 permits entry of textual information into host computer 602, as known within the art, and embodiments are not limited to any particular type of keyboard. Pointing device 620 permits the control of the screen pointer provided by a GUI of operating systems such as versions of Microsoft Windows®. Embodiments are not limited to any particular pointing device 620. Such pointing devices include mice, touch pads, trackballs, remote controls and point sticks. Other input devices (not shown) can include a microphone, joystick, game pad, satellite dish, scanner, or the like.

In some embodiments, host computer 602 is operatively coupled to a display device 622. Display device 622 is connected to the system bus 612. Display device 622 permits the display of information, including computer, video and other information, for viewing by a user of the computer. Embodiments are not limited to any particular display device 622. Such display devices include cathode ray tube (CRT) displays (monitors), as well as, flat panel displays such as liquid crystal displays (LCD's). In addition to a monitor, computers typically include other peripheral input/output devices such as printers (not shown). Speakers 624 and 626 provide audio output of signals. Speakers 624 and 626 are also connected to the system bus 612.

Host computer 602 also includes an operating system (not shown) that is stored on the computer-accessible media RAM 606, ROM 608, and mass storage device 610, and is executed by the processor 604. Examples of operating systems include Microsoft Windows®, Apple MacOS®, Linux®, UNIX®. Examples are not limited to any particular operating system, however, and the construction and use of such operating systems are well known within the art.

Embodiments of host computer 602 are not limited to any type of host computer 602. In varying embodiments, host computer 602 comprises a PC-compatible computer, a MacOS®-compatible computer, a Linux®-compatible computer, or a UNIX®-compatible computer. The construction and operation of such computers are well known within the art.

Host computer 602 can be operated using at least one operating system to provide a GUI including a user-controllable pointer. Host computer 602 can have at least one web browser application program executing within at least one operating system, to permit users of host computer 602 to access intranet or Internet world-wide-web pages as addressed by Universal Resource Locator (URL) addresses. Examples of browser application programs include Netscape Navigator® and Microsoft Internet Explorer®.

Host computer 602 can operate in a networked environment using logical connections to one or more remote computers, such as wired communication path 106. These logical connections are achieved by a communication device that is coupled to, or is a part of, the host computer 602. Embodiments are not limited to a particular type of communications device.

The logical connections depicted in FIG. 6 include a local-area network (LAN) 630 and a wide-area network (WAN) 632. Such networking environments are commonplace in offices, enterprise-wide computer networks, intranets and the Internet. When used in a LAN-networking environment, the host computer 602 is connected to the local network 630 through network interface circuitry (NIC) 634 and 636. A NIC is one type of communications device 616. When used in a conventional WAN-networking environment, the host computer 602 communicates to the portable X-ray detector 104 through a WAN 632 using a modem (not shown). The modem, which can be internal or external, is connected to the system bus 612. In a networked environment, program modules depicted relative to the host computer 602, or portions thereof, can be stored in the portable X-ray detector 104.

Host computer 602 includes power supply 638. Power supply 638 can be derived from an alternating current source, such as a standard wall outlet, or from a battery. Power supply 638 serves as a power source for host computer 602. Power supply 638 can also serve as a power source for portable X-ray detector 104 and/or as a charging power source for portable X-ray detector 104, e.g., when LAN connection 630 includes a power connection.

Alternatively, the portable X-ray detector 104 can include power supply 638. Power supply 638 can be derived from an alternating current source, such as a standard wall outlet, or from a battery. Power supply 638 can serve as a charging power source for portable X-ray detector 104.

CONCLUSION

A portable imaging system, apparatus and methods of use have been described. Although specific embodiments are illustrated and described herein, any arrangement which is calculated to achieve the same purpose may be substituted for the specific embodiments shown. This application is intended to cover any adaptations or variations. For example, although described in medical imaging terms, it should be appreciated that implementations can be made in an industrial or any other secured environment that provides the required relationships.

In particular, the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. Embodiments are applicable to future medical devices, different imaging systems, and new data types.

The terminology used in this application with respect to the portable imaging technology is meant to include all data objects and network environments and alternate technologies that provide the same functionality as described herein.

We claim:

1. A portable imaging device comprising:
   a processor;
   a memory operably coupled to the processor;
   a detector connection point operably coupled to the processor and operable to communicate data through a wired communication path the data further comprising image data; and
   a wireless transceiver operably coupled to the processor and operable to communicate data with a digital medical diagnostic imaging system through a wireless communication path,
   wherein the image data further comprises high-resolution images and low-resolution images,
   wherein the processor is operable to withhold the high-resolution images from transmission through the wired communication path, the processor is operable to transfer nearly immediately the low-resolution images through the wireless communication path and the processor is operable to store the high-resolution images to the memory until the wired communication path is active, and the processor is operable to the high-resolution images through the wired communication path upon activation of the wired communication path.

2. The portable imaging device of claim 1, wherein the wireless communication path further comprises:
   an Ethernet protocol wireless communication path.

3. The portable imaging device of claim 1, wherein the wired communication path further comprises:
   an Ethernet protocol wired communication path.

4. The portable imaging device of claim 1, wherein the at least one portable imaging device further comprises:
   a portable X-ray detector.

5. The portable imaging device of claim 1, wherein the low-resolution images data further comprises:
   reduced spatial resolution image data.

6. The portable imaging device of claim 1, wherein the data further comprises:
   wireless communication configuration data.

7. The portable imaging device of claim 6, wherein the wireless communication configuration data further comprises:
   one or more of operating frequency, encryption keys and network identification.

8. An imaging system comprising:
   a digital medical diagnostic imaging system; and
   at least one portable imaging device operable to communicate data with the digital medical diagnostic imaging system through at least one of a wired communication path, and a wireless communication path, wherein the data further comprises image data, wherein the image data further comprises high-resolution images and low-resolution images, the least one portable imaging device is operable to store the high-resolution images until the wired communication path is active, and the least one portable imaging device is operable to transfer nearly immediately the low-resolution images through the wireless communication path.

9. The imaging system of claim 8, wherein the direct wired communication path further comprises:
   a 802.3z gigabit Ethernet protocol.

10. The imaging system of claim 8, wherein the at least one portable imaging device further comprises:
    a portable X-ray detector.

11. The imaging system of claim 8, upon the condition in which the wired communication path is not established, not accepting charging power for a rechargeable power supply in the portable imaging device.

12. The imaging system of claim 8, wherein the data comprises wireless communication configuration data.

13. The imaging system of claim 12, wherein the wireless communication configuration data relates to one or more of operating frequency, encryption keys and network identification.

14. A method for communicating data between a portable imaging device and a digital medical diagnostic imaging system, the method comprising:
   determining whether a wired communication path is established between the portable imaging device and the digital medical diagnostic imaging system;
   upon a condition in which the wired communication path is established, using the wired communication path to communicate the data between the portable imaging device and the digital medical diagnostic imaging system, wherein the data further comprises image data, wherein the image data further comprises high-resolution images and low-resolution images; and
   upon a condition in which the wired communication path is not established:
      establishing a wireless communication path between the portable imaging device and the digital medical diagnostic imaging system; and
      using the wireless communication path to communicate only the low-resolution images from the memory between the portable imaging device and the digital medical diagnostic imaging system.

15. The method of claim 14, further comprising:
   upon the condition in which the wired communication path is established, sending wireless communication configuration data from the digital medical diagnostic imaging system to the portable imaging device for subsequent use in a wireless communication path.

16. The method of claim 15, wherein the wireless communication configuration data sent from the digital medical diagnostic imaging system to the portable imaging device relates to one or more of operating frequency, encryption keys and network identification.

17. The method of claim 14, further comprising:
   upon the condition in which the wired communication path is not established, not accepting charging power for a rechargeable power supply in the portable imaging device.

18. The method of claim 14, further comprising:
   upon the condition in which the wired communication path is established, accepting charging power for a rechargeable power supply in the portable imaging device.

19. The method of claim 18, upon the condition in which the wired communication path is not established, not accepting charging power for a rechargeable power supply in the portable imaging device.

20. The method of claim 14, wherein the portable imaging device further comprises a portable X-ray detector.

21. The method of claim 20, wherein the data further comprises a subset of image data.

22. The method of claim 21, wherein subset further comprises at least one image selected from the group of images consisting of a reduced number of images, a plurality images composed of reduced spatial resolution, and a plurality of pixels of reduced bit depth.

23. The method of claim 14, further comprising:
   upon the condition in which the wired communication path is established, signaling to the computer that the wired communication path is going to be severed.

* * * * *